(12) United States Patent
Yuds et al.

(10) Patent No.: US 11,160,913 B2
(45) Date of Patent: Nov. 2, 2021

(54) REMOVAL OF MICROBUBBLES THROUGH DRIP CHAMBER NUCLEATION SITES

(71) Applicant: Fresenius Medical Care Holdings, Inc., Waltham, MA (US)

(72) Inventors: David Yuds, Antioch, CA (US); Martin Joseph Crnkovich, Concord, CA (US); Colin Weaver, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 457 days.

(21) Appl. No.: 16/168,852

(22) Filed: Oct. 24, 2018

(65) Prior Publication Data

US 2019/0143023 A1 May 16, 2019

Related U.S. Application Data

(60) Provisional application No. 62/585,838, filed on Nov. 14, 2017.

(51) Int. Cl.
| | | |
|---|---|---|
| *A61M 1/36* | (2006.01) | |
| *B01D 19/00* | (2006.01) | |
| *A61M 5/168* | (2006.01) | |
| *A61M 5/14* | (2006.01) | |

(52) U.S. Cl.
CPC .......... *A61M 1/3627* (2013.01); *A61M 5/168* (2013.01); *B01D 19/0073* (2013.01); *A61M 5/1411* (2013.01); *A61M 2207/00* (2013.01)

(58) Field of Classification Search
CPC .. A61M 1/3627; A61M 5/1411; A61M 5/168; B01D 19/0073
See application file for complete search history.

(56) References Cited

U.S. PATENT DOCUMENTS

| | | |
|---|---|---|
| 3,775,339 A | 11/1973 | Kasulin et al. |
| 3,961,918 A | 6/1976 | Johnson |
| 4,334,988 A | 6/1982 | Milligan |

(Continued)

FOREIGN PATENT DOCUMENTS

WO 9711729 4/1997

OTHER PUBLICATIONS

Keshavarzi G. et al. "Two-dimensional computational analysis of microbubbles in hemodialysis," Wiley Periodicals, Inc. and International Center for Artificial Organs and Transplantation (2013); vol. 37, issue 8; Abstract Only.

(Continued)

*Primary Examiner* — Kai H Weng
(74) *Attorney, Agent, or Firm* — Kilyk & Bowersox, P.L.L.C.

(57) ABSTRACT

A drip chamber is provided that includes a hollow body and a nucleation column extending into the interior of the hollow body. The nucleation column can be formed with, or treated by a treatment to include, microfeatures or other surface properties that provide nucleation sites for the nucleation and amalgamation of microbubbles. The drip chamber can include a bubble catcher in the bottom of the hollow body and the nucleation column can extend from the bubble catcher into the interior of the hollow body. Methods of making such drip chambers are also provided.

6 Claims, 4 Drawing Sheets

(56) References Cited

U.S. PATENT DOCUMENTS

| | | | | |
|---|---|---|---|---|
| 4,664,682 | A * | 5/1987 | Monzen | A61M 1/3627 128/DIG. 3 |
| 5,328,461 | A * | 7/1994 | Utterberg | A61M 1/3627 210/239 |
| 5,980,741 | A | 11/1999 | Schnell et al. | |
| 6,010,623 | A | 1/2000 | Schnell et al. | |
| 8,430,834 | B2 | 4/2013 | Kopperschmidt | |
| 8,852,135 | B2 | 10/2014 | Beden et al. | |
| 9,316,523 | B2 | 4/2016 | Schneider et al. | |
| 2002/0029021 | A1 | 3/2002 | Bormann et al. | |
| 2010/0055003 | A1* | 3/2010 | Swanson | B05B 17/04 422/168 |
| 2012/0152787 | A1 | 6/2012 | Reiter et al. | |
| 2014/0283684 | A1 | 9/2014 | Zahka et al. | |
| 2017/0021385 | A1* | 1/2017 | Smith | C08J 7/043 |

OTHER PUBLICATIONS

Wagner, Stephan et al. "Observation of microbubbles during standard dialysis treatments," Clinical Kidney Journal (2015), vol. 8, No. 4, pp. 400-404.

International Search Report (Form PCT/ISA/210) for International Patent Application No. PCT/US2018/057196, dated Jan. 29, 2019, including the Written Opinion of the International Searching Authority (Form PCT/ISA/237), separate sheets, and Information on Search Strategy (14 pages).

\* cited by examiner

REMOVAL OF MICROBUBBLES THROUGH DRIP CHAMBER NUCLEATION SITES

This application claims the benefit under 35 U.S.C. § 119(e) of prior U.S. Provisional Patent Application No. 62/585,838, filed Nov. 14, 2017, which is incorporated in its entirety by reference herein.

BACKGROUND

During the course of hemodialysis, defects in the extracorporeal blood circuit can allow air to enter the bloodstream. For this purpose, a hemodialysis machine contains an air detector, a level detector, and a bubble catcher in a venous drip chamber.

Miniscule amounts of air, for example, less than 200 µm, can be released into the bloodstream as microbubbles. Most bubble catchers in venous drip chambers are totally ineffective at capturing bubbles less than 50 µm. Microbubbles of such small size cannot be filtered out or trapped by a bubble catcher because using a screen small enough for such filtering would impede blood flow. New research shows that microbubbles are a cause for concern. Microbubbles have been linked to lung injuries and damage to the brain in hemodialysis patients, as described in the National Institutes of Health publication https://www.ncbi.nlm.nih.gov/pubmed/23826686.

Bubble catchers are known for separating air bubbles from blood, for example, from U.S. Pat. No. 3,961,918 to Johnson, U.S. Pat. No. 4,334,988 to Milligan, U.S. Pat. No. 5,980,741 to Schnell et al., U.S. Pat. No. 6,010,623 to Schnell et al., U.S. Pat. No. 8,430,834 B2 to Kopperschmidt; U.S. Pat. No. 8,852,135 to Beden et al., and U.S. Pat. No. 9,316,523 B2 to Schneider et al., each of which is incorporated herein in its entirety by reference.

Despite many different designs, a need still exists for a drip chamber that provides a means for microbubbles to collect and amalgamate into larger bubbles that can rise to a blood/air interface in the drip chamber or be easily trapped and prevented from entering a venous blood return line.

SUMMARY

The present invention provides a drip chamber that more effectively separates and captures microbubbles compared with conventional drip chambers. The drip chamber provides sites for microbubbles to collect and amalgamate into larger bubbles that can rise to the blood/air interface in the chamber or be easily trapped and prevented from entering a venous blood return line. According to various embodiments, the drip chamber comprises a hollow body having a top and a bottom, an inlet in fluid communication with the hollow body, an outlet in fluid communication with the hollow body at the bottom of the hollow body, and a nucleation column extending into the interior of the hollow body. The nucleation column has an outer surface and can have any of a variety of cross-sectional shapes, for example, square, polygonal, circular, ring-shaped, triangular, star-shaped, and the like. The hollow body can be defined by a sidewall that defines the interior. The nucleation column can be formed with, or treated by a treatment to include, microfeatures or other surface properties that provide nucleation sites for the nucleation and amalgamation of microbubbles in a liquid that contacts the outer surface, for example, blood.

The nucleation column provides abundant and/or efficient nucleation sites for promoting microbubble attachment and amalgamation. The drip chamber can be free of a nucleation column and the inner surface can instead be provided with abundant and/or efficient nucleation sites. Information about nucleation sites and how they work can be found at https://www.quora.com/What-are-nucleation-sites-and-how-do-they-work, which is incorporated herein in its entirety by reference.

The drip chamber can further comprise a bubble catcher in the bottom of the hollow body. The bubble catcher can provide flow passages that provide fluid communication between the interior of the hollow body and the outlet. The nucleation column can extend from the bubble catcher into the interior of the hollow body.

Figure 1:
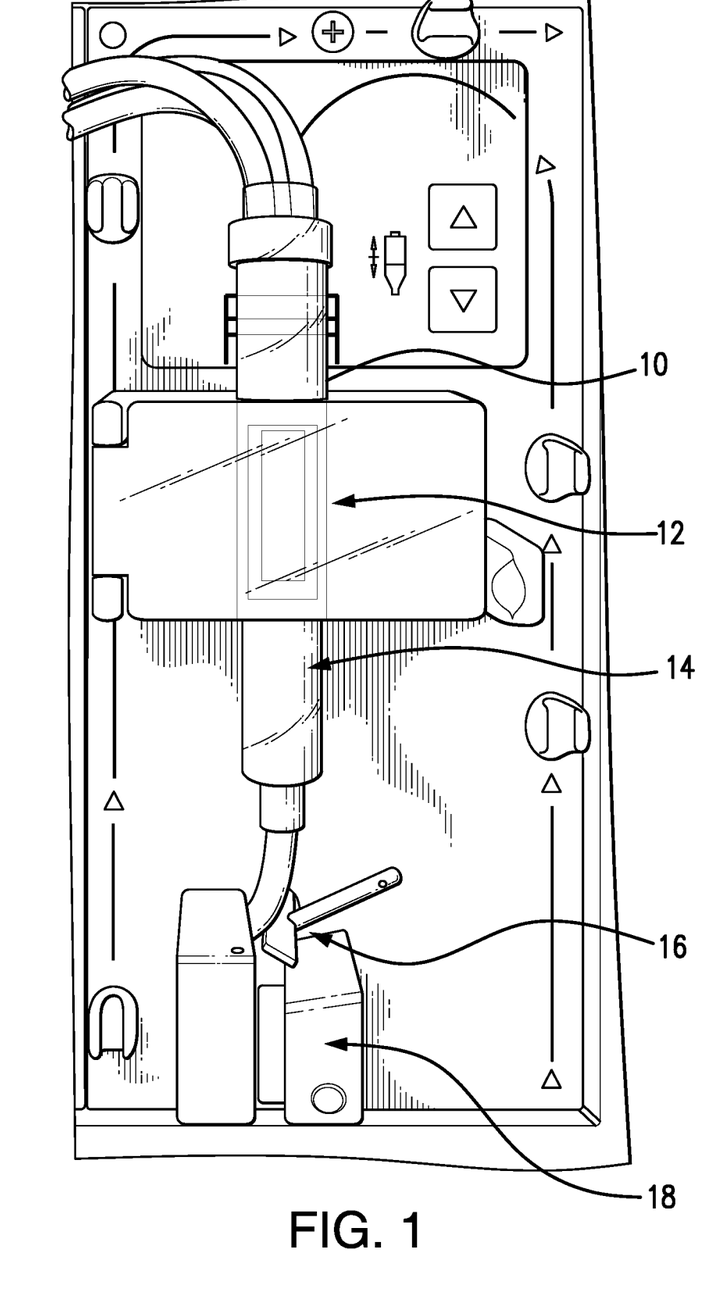
FIG. 1 is a photograph showing a venous module for capturing air in a blood circuit.

The drip chamber can be used in a hemodialysis machine such as shown in FIG. 1. The hemodialysis machine can include a drip chamber 10, a level detector 12 for detecting the level of blood in drip chamber 10, a bubble catcher 14, a venous clamp 16, and an optical bubble detector 18. According to the present invention, the drip chamber can be formed with, or treated to provide, nucleation sites for the attachment and amalgamation of microbubbles.

Figure 2:
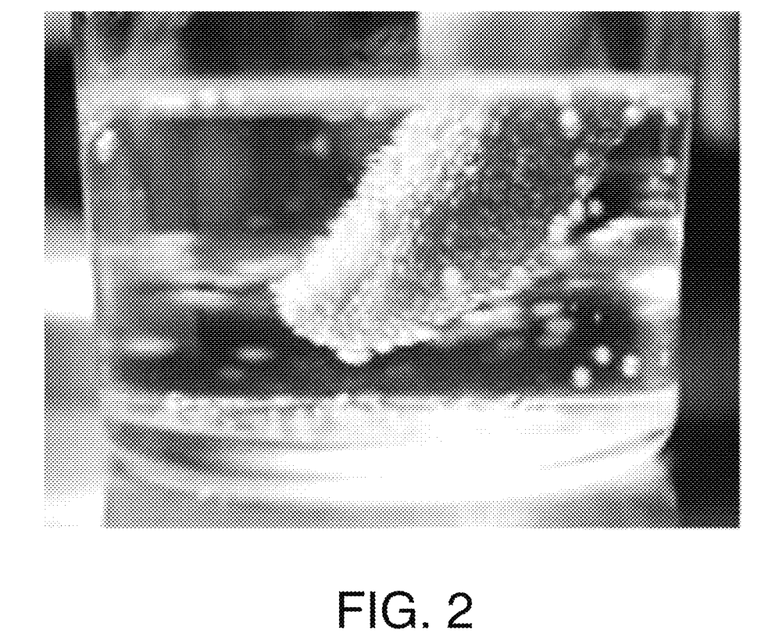
FIG. 2 is a photograph showing nucleation occurring on a fingertip submerged in a liquid.
Figure 3:
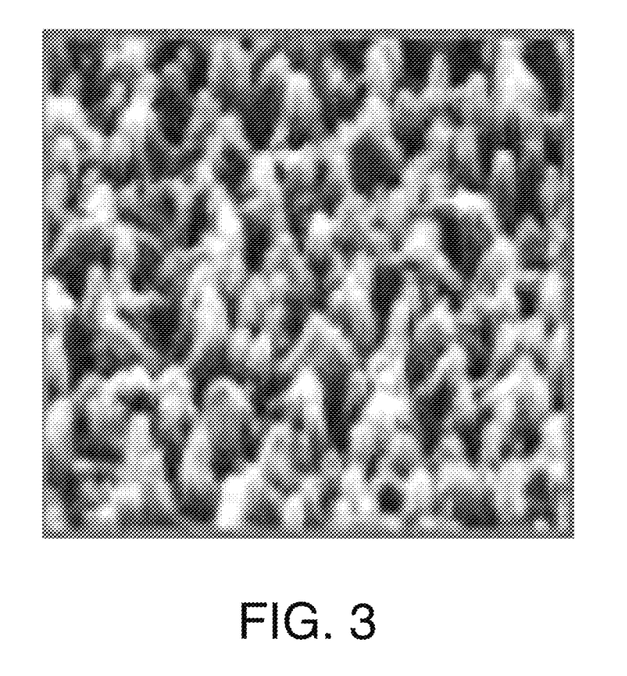
FIG. 3 is a microphotograph showing features on an irregular surface, under an electron microscope.

Nucleation sites are microscopic features or imperfections on or in surfaces that allow bubbles to hold on. FIG. 2 shows an example of nucleation occurring at a fingertip submerged in liquid where the irregular surface of the finger enables bubbles to stick. Creating an irregular inner surface in a venous drip chamber, for example, as shown in FIG. 3, by providing additional surface area, surface features, and/or surface properties, can be used to capture, that is, make stick, more and smaller microbubbles.

Figure 4A:
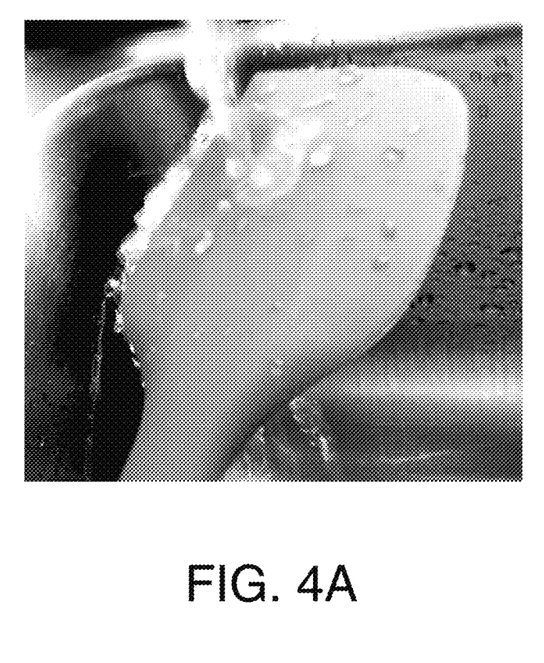
FIG. 4A is a photograph showing a plastic utensil surface catching air bubbles from a flow of water.
Figure 4B:
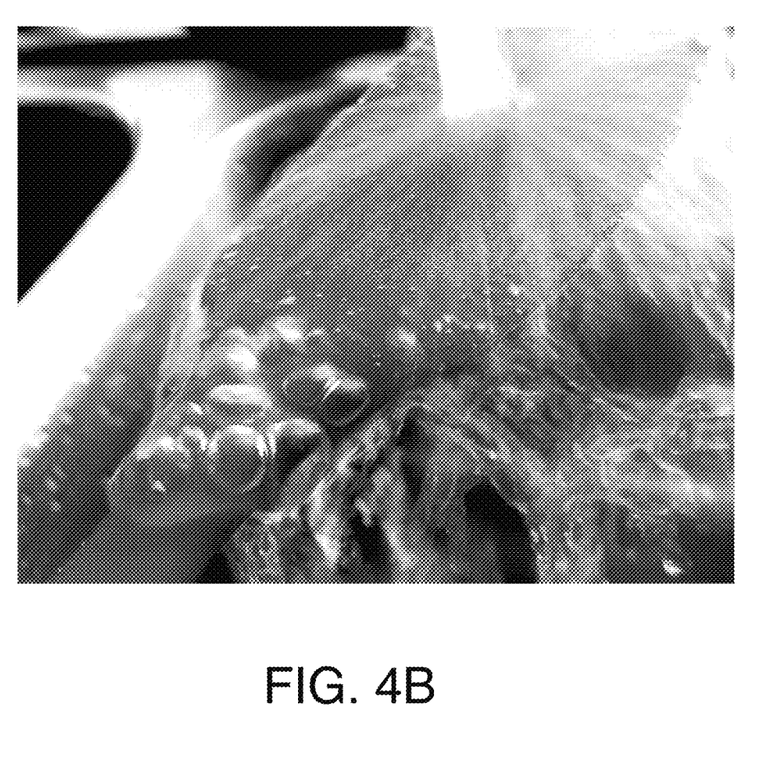
FIG. 4B is an enlarged photograph of the plastic utensil shown in FIG. 4A and showing how bubbles on the surface amalgamate into larger bubbles.

FIG. 4 further demonstrates this principle on a silicon surface that appears smooth but catches air microbubbles in a flow of water flowing across the surface. The surface also enables captured microbubbles to amalgamate into larger bubbles that can then be strained out by a bubble catcher.

Figure 5:
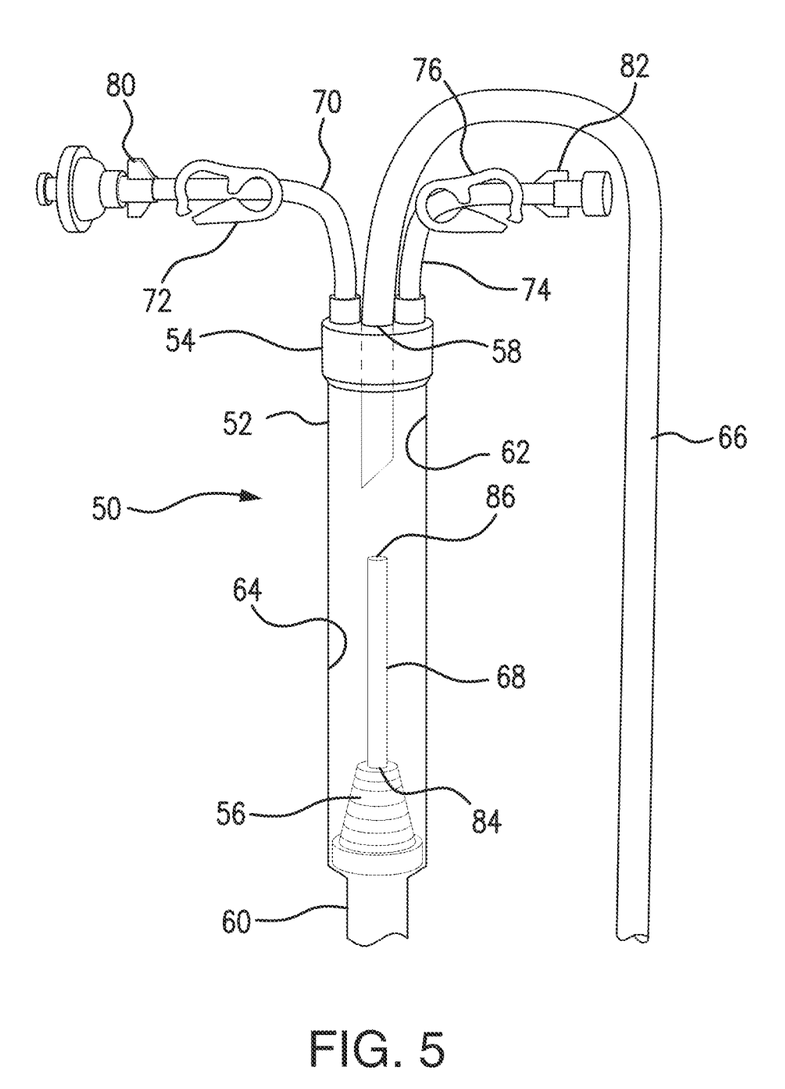
FIG. 5 is a front view of a drip chamber comprising a bubble catcher in the bottom of the drip chamber, a nucleation column, a blood tube going into the drip chamber, a pressure transducer tube in fluid communication with and leading away from the headspace in the drip chamber, and a medication port tube leading into the drip chamber.

According to various embodiments, a nucleation column is created in the venous drip chamber by providing the bubble catcher with a nucleation column attached. The bubble catcher can itself be provided with a microscopically rough surface, as shown in FIG. 5. FIG. 5 is described in greater detail below. In the example shown in FIG. 5, the blood, on its way back to the patient, flows into the venous drip chamber where a combination of turbulence and irregular surfaces collect and grow microbubbles into bubbles of a size that can rise to the blood/air interface or readily be filtered out.

While improving bubble detectors can be important, attacking the problem of microbubbles themselves and preventing them from ever reaching the final safeguard of a bubble detector is an even more effective way of obviating the problem.

DETAILED DESCRIPTION

According to various embodiments, a drip chamber having a nucleation column is provided having abundant and efficient nucleation sites to promote microbubble attachment and amalgamation. The nucleation column can be formed of a material comprising plastic, glass, or the like. The nucleation column can be formed to extend into the interior of the drip chamber. It can be mounted at or near the top, the bottom, a side, or a sidewall of the drip chamber. The inner surface of the drip chamber, the nucleation column, or both, can be treated or formed to provide the nucleation sites. When treated, the material can exhibit more and/or more effective nucleation sites compared with the same material under the same conditions but that has not been treated. The surface of the nucleation column, inner surface, or both, can be molded to include, or treated to provide, surface features providing nucleation sites.

The surface features formed on the surface can be textured, patterned, sintered, sanded, sand-blasted, etched, porous, rough, pitted, foamed, grooved, cross-hatched, striated, or otherwise formed to promote nucleation and amalgamation of trappable gas bubbles from microbubbles in the drip chamber. The material of each of the nucleation column and the drip chamber sidewall can independently be transparent, translucent, opaque, or non-transparent and the drip chamber itself can be transparent, translucent, opaque, or non-transparent. In addition to, or as an alternative to, texturing, the nucleation column and/or drip chamber sidewall can be coated on a surface thereof, with a coating material that forms a coating exhibiting abundant and efficient nucleation sites, that is, having improved nucleation efficiency relative to the same surface but without the coating. The sites promote the nucleation of microbubbles and amalgamation thereof to form gas bubbles that are large enough to rise to the blood/air interface or be trapped by a drip chamber bubble catcher or bubble trap. Particular materials that can be coated include those having a surface comprising plastic, sintered material, textured material, glass, ceramic, metal, or a primed or pre-coated surface. A smooth surface can be coated with a coating that provides nucleation sites in the form of surface features. A coating that provides abundant and efficient nucleation sites can be provided on surfaces that are porous, smooth, rough, pitted, foamed, grooved, cross-hatched, striated, or that otherwise have, or lack, patterned or non-patterned physical features.

The nucleation efficiency of the inner surface coating depends on a number of factors including the material of the drip chamber that is coated and the type, amount, and population of chemical groups present on the exposed surface of the coating. An improvement of 5% or more, in the number of nucleation sites, represents an improved nucleation efficiency, although improvements in surface populations of nucleation sites of 10% or more, 20% or more, 30% or more, or 50% or more can be provided and/or considered an improvement in nucleation efficiency, that is, to be considered to have improved nucleation efficiency. Regardless of any increase in population, or factored together with an increase in population, nucleation efficiency can be measured as increased microbubble production and release. The increased production can be measured optically, for example, by measuring production from a calibrant, microbubble-containing mixture, such as blood. Improvements in the form of increased microbubble production of 5%, 10%, 20%, 30%, 50%, or more can be considered to represent an improvement in nucleation efficiency.

Methods of forming surface features that can be useful as nucleation sites can depend on the material used for the drip chamber. Tooling or machining can be used to form surface features on the nucleation column or inner surface of the drip chamber. The nucleation sites can be provided on both the nucleation column and the drip chamber inner surface. Exemplary methods include embossing, scratching, machining, micromachining, sanding, sand-blasting, channeling, pitting, ablating, melting, sintering, heat-treating, laser-treating, chiseling, drilling, and like methods, and combinations thereof.

Chemical treatment methods can be used to form surface features on the nucleation column or inner surface of the drip chamber. Chemical solvents or chemical etchants can be used to etch, partially dissolve, or otherwise deform, degrade, or roughen the surface to form physical microfeatures thereon or therein. Any suitable etchant that can be matched to the nucleation column material or drip chamber material can be used to control the amount and/or rate of surface treatment. As an example, an aggressive etchant can be used on more robust materials. Tetra-Etch® fluorocarbon etchant, available from Polytetra of Monchengladbach, Germany, can be used, for example, to etch fluorocarbon materials such as those comprising polytetrafluoroethylene and other fluorocarbons. Acid etchants can be used to etch silica materials and other materials, including, for example, polysulfone, polyvinylchloride, polyvinylidene, and polycarbonate. Nucleation columns and drip chambers made of Biofine® (available from Fresenius Medical Care Deutschland GmbH of Bad Homburg, Germany) and other polyolofine materials can be used and can be etched with acid etchants and the like. Biofine® is a preferred material for a nucleation column because of its biocompatibility and its ability to be stream sterilized at a temperature of 121° C. Both the nucleation column and the inner surface can comprise the same material and can be etched with the same or different etchants.

Nucleation columns and drip chamber inner surface can be molded, for example, by processes that themselves result in the formation of surface features providing nucleation sites. Extrusion molding, spinning, melt-spinning, co-extrusion, and other molding methods can be used.

According to various embodiments, the bubble catcher in the drip chamber can be made of the same material as the nucleation column, drip chamber, both, or any other material as described herein. Like the nucleation column, the bubble catcher can also comprise nucleation site-forming surface features formed thereon as described herein.

Drip chambers according to the present invention can have at least one nucleation site surface. The drip chamber can have at least one interior wall that defines a reservoir portion for containing a volume of liquid, specifically, blood, and at least one opening in communication with the reservoir portion. According to various embodiments, the drip chamber is coated on its inner surface, or interior wall, and on the area surrounding and forming the opening, with a polymer coating that provides nucleation sites.

Exemplary materials that can be used to manufacture the drip chambers of the present invention, for example, those including a nucleation column, include polypropylene, polyethylene, polyethyleneterephthalate, polystyrene, polycarbonate, and cellulosics. More expensive plastics such as polytetrafluoroethylene and other fluorinated polymers can be used. Some drip chambers made from these plastics are hydrophobic without any additional coating. Herein, the term "hydrophobic" refers to a surface exhibiting an average surface energy of about 40 dynes/cm or less. While hydrophobic inner surfaces are desired as blood will not cling to the surface, extremely hydrophobic surfaces, i.e., having surface energies of 20 dynes/cm or less, may not be desired because gas bubbles tend not to cling to such surfaces and do not tend to amalgamate into trappable microbubbles. Polypropylene is inexpensive and quite hydrophobic itself, and can be used as a material for the nucleation column and/or drip chamber sidewall of the present invention.

In addition to the materials mentioned above, examples of other suitable materials for the nucleation column and/or drip chamber sidewall include polyolefins, polyamides, polyesters, silicones, polyurethanes, epoxies, acrylics, polyacrylates, polyesters, polysulfones, polymethacrylates, polycarbonate, PEEK, polyimide, polystyrene, and fluoropolymers such as PTFE Teflon®, FEP Teflon®, Tefzel®, poly(vinylidene fluoride), PVDF, and fluoroalkoxy resins. Glass products including silica glass can also be used to manufacture the nucleation columns and/or drip chamber sidewall. One exemplary glass product is PYREX® (available from Corning Glass, Corning, N.Y.). Coated surfaces of glass, silicon, silicon compounds, and ceramics that have or have not been primed with silane-containing materials or other adhesion promoting materials can also be used. Primed glass, primed ceramic, and primed oxide surfaces can be coated to form the nucleation column and/or drip chamber sidewall according to various embodiments. Surfaces that have been pre-coated with epoxies, silicones, urethanes, acrylics, or other materials can be coated to form the nucleation column and/or drip chamber sidewall according to various embodiments of the invention.

The nucleation column exposed surface and/or drip chamber inner surface can have any suitable surface energy but surface energies of from about 35 dynes/cm to about 60 dynes/cm can be preferred. Materials providing higher or lower surface energies can also be used. An exemplary range of preferred surface energies can be the range of from about 39 dynes/cm to about 46 dynes/cm.

According to various embodiments, the inner surface of the drip chamber is at least partially coated with a coating formulation. A delineated area of the inner surface can be free of, that is, not coated with, the coating formulation, but can instead be surrounded by the coating. The coating thus forms a boundary to promote the nucleation of bubbles at only certain areas of the drip chamber. The uncoated locations may have surfaces that, for example, have specific affinities, optimize the sample volume to area ratio, or restrict gas bubbles movement. The uncoated region may be surrounded by a hydrophobic coating material, for example, comprising microparticles. According to various embodiments, the inner surface of the drip chamber can be partially coated with a hydrophobic coating formulation and partially coated with non-fluorinated material in delineated regions.

According to various embodiments, the inner surface of the drip chamber can be provided with a first coating and a second coating. The second coating can comprise the reaction product, for example, the polymerization product, of a second reactant, for example, a fluorinated monomer. The second reactant can have, for example, from about 3 to about 20 carbon atoms, and can be combined with a surface roughening agent, for example, a micropowder that provides the second coating with a rough surface and abundant nucleation sites.

In various embodiments, microscopic fibers such as cellulose or glass microfibers can be used with, or in place of, microparticles to provide surface roughness and nucleation sites. Preferably, cellulose and/or glass microfibers are used that have average diameters of from about one to about 100 microns and lengths of from about 20 to several hundred microns. The microfibers can be admixed to increase the mechanical strength of the coating.

According to various embodiments, rough surfaces providing good nucleation sites can be produced by employing foaming and/or pore-forming agents in the coating compositions. Foaming and pore-forming agents that may be used include spirocarbonates, diazo compounds, compressed gases, dissolved gases, volatile liquids, and combinations thereof. The agents may be activated by heat, light, or vacuum during the drying, curing, and/or hardening of the coating composition.

According to various embodiments, nucleation sites on the nucleation column or on the inner surface of a drip chamber can be formed from a coating formulation comprising microparticles and the reaction product of a monomeric reactant. The microparticle-containing coating provides nucleation sites for the attachment of and amalgamation of microbubbles.

In various embodiments, a coating is provided by adhering to a surface roughening agent, for example, a micropowder, to the surface of a reaction product, wherein the coating has an exposed surface area populated with 5% or more fluoromethyl groups. A coating can be formed with a surface roughening agent having a surface area populated with 5% by area or more trifluoromethyl groups, wherein the surface roughening agent is adhered to the hydrophobic surface. The adherence of the surface roughening agent to the surface may be due to one or more mechanisms including, but not limited to, sintering the agent onto the surface, curing a component of the surface and/or of a component of the agent, melting the surface and/or the agent, using like methods, or any combination thereof. The surface roughening agent, for example, a micropowder, can be dusted onto the surface.

The present invention also provides processes of preparing surface roughening agent-containing surfaces. According to various embodiments, a coating formulation is applied to the nucleation column or to the inner surface of the drip chamber to form a coating having an exposed surface area exhibiting a surface energy of from about 35 dynes/cm to about 60 dynes/cm, for example, from about 39 dynes/cm to about 46 dynes/cm. Then, fluidized surface roughening agent microparticles are applied and adhered to the coating to provide a rough surface. The adherence of the agent to the coating may be due to one or more mechanisms including, but not limited to, sintering the agent onto the surface, curing a component of the coating and/or a component of the agent, melting the coating and/or the agent, by like methods, or any combination thereof.

The coating composition can be diluted with an appropriate solvent or medium to obtain a coating solids content, or a non-volatile components content, of from about 0.01% by weight to about 50% by weight, for example, from about 0.1% by weight to about 2% by weight, depending upon the application technique and desired coating properties.

Lower surface tensions can be obtained when the coating polymer comprises the polymerization product of a fluoroalkyl monomer or a perfluoroalkyl monomer, when compared to coatings comprising the product of a non-fluorinated or mostly non-fluorinated monomer. Substantially non-branched alkyl ethylenically unsaturated monomers can be used to produce surfaces exhibiting surface tensions of from about 30 dynes/cm to 60 dynes/cm and that provide good nucleation sites. Materials and coatings that provides surface energies of from about 35 dynes/cm to about 55 dynes/cm, or from about 39 dynes/cm to about 46 dynes/cm, can be preferred according to various embodiments. A methacrylate group can be used as an ethylenically unsaturated monomer for making a coating on the nucleation column or on the drip chamber sidewall. Other monomers that can be used include silicones, epoxies, and urethanes. Other reactants that can be used include anhydrides, amines, polyols, vinyls, vinyl ethers, and mixtures thereof. Polymers made from mixtures of acrylates and epoxies, or of acrylates and silicones, can be used. According to various embodiments, the nucleation column or the drip chamber inner surface can be provided with a coating thereon, and optionally a durable resinous component such as a urethane or polyurethane component. Coating solutions can be used at full strength but may be diluted, for example, with a fluorosolvent, to form low concentrations of coating polymer. The polymer solution used to make the coatings can have a coating polymer content of from about 0.01% by weight to about 50% by weight.

Additives can be incorporated into or polymerized with the coating polymers and monomers used to provide coatings having improved toughness, chemical resistance, hardness, softness, processability, elasticity, adhesion, color, texture, thickness, and/or ultraviolet (UV)-resistance. Hydrophilic additives can be used and can provide attachment surfaces in the form of nucleation sites to attract, attach, and amalgamate microbubbles. Channels having gradients of hydrophobicity to hydrophilicity can be provided to channel, move, and direct microbubbles together or toward a common microbubble amalgamation location where they can merge together to become a single, larger, trappable microbubble. Grooves having different coating materials, a gradient of coating, thicknesses, or both, can be used, for example, to form such channeling features. Chemically resistant additives can be used. Additives including reactants and/or monomers can be added in amounts ranging from 1% by weight to about 95% by weight and are described in more detail below.

Coating compositions can be used that combine nucleation site-forming particles and chemically resistant non-fluorinated resins such as acrylics, cellulosics, epoxy, polyesters, silicones, urethanes, anhydrides, amines, polyols, vinyls, vinyl ethers, and combinations thereof. These mixtures can produce surfaces exhibiting any of a range of surface energies and abundant nucleation sites.

According to various embodiments, the coating composition can comprise an aromatic or aliphatic polyurethane. The coating can comprise the polymerization product of an isocyanate-containing monomer. The coating can further comprise a cellulosic, a polyester, the polymerization product of an unsaturated monomer, a condensation polymer, a silicone polymer, an epoxy, or a combination thereof.

According to various embodiments, hydrophobic coatings are made of a polymerization product of a fluorinated monomer and a small amount of a co-monomer, for example, a silane, that serves to promote adhesion of the coating to the nucleation column or drip chamber inner surface without compromising the surface energy of the coating. Coupling agents can also be used as adhesion promoting monomers. Such silanes and coupling agents, if present, can be present in amounts of from 1% by weight to about 10% by weight, or from about 2% by weight to about 5% by weight.

Aqueous suspension formulations that can be used can include additives as discussed above, including epoxy resins. Exemplary waterborne epoxy resins that can be used in aqueous suspension coating formulations include the EPI-REZ Resins from Shell Chemical Company, for example, the EPI-REZ Resins WD-510, WD-511, WD-512, 3510-W-60, 3515-W-60, 3519-W-50, 3520-WY-55 and 3522-W-60. The coating composition can comprise microparticles, microfibers, foaming and/or pore-forming agents, and can be dried, cured, and/or hardened so as to produce sufficient surface roughness to provide abundant nucleation sites.

Another method of forming a coating for use on the nucleation column or drip chamber inner surface is by using monomers capable of free radical linkages. Such monomers can be attached to the nucleation column or inner surface of the drip chamber if the surface is first treated by ionizing radiation or other means to generate free radicals across the surface. A monomer capable of free radical linkages can be formed by mixing an alkyl ethylenically unsaturated monomer dissolved in a suitable solvent, with an effective amount of a free radical initiator. A nucleation column, for example, made of glass, can be coated with the mixture are then heated to the temperature at which the free radical initiator initiates free radical generation. Many conventional azo compounds have an appropriate activation temperature, particularly within the range of from 30° C. to 200° C. Many azo compounds can be used which are activated by visible or UV light.

A microscopically roughened or porous surface can be made by adding microscopic particles of a surface roughening agent, for example, micropowder, to the coating material or to the surface to which the coating formulation is to be applied.

Many microparticles can be used as surface roughening agents to form nucleation sites, including micropowders. Micropowders are defined herein as those powders or particles having average diameters of from submicron sizes up to 100 microns. An exemplary micropowder average diameter is about 10 microns or less. Suitable micropowders include silicon glass particles with and without silane coatings, pigments, Teflon® powders, siliconized glass, fluorosiliconized inorganic pigments, and micronized cellulosics. According to various embodiments, a composite surface can be formed by adding a substantially uniformly sized micropowder to a polymer or a monomer that is to be subsequently applied as a coating and then polymerized. The use of micropowders exhibiting wide particle size distributions can also be used to provide a coating providing an abundance of different nucleation sites.

Inert micropowders can be used. One exemplary micropowder is a siliconized glass particulate material having a 0.3 micron average particle size diameter available as TULLANOX HM 250 or TULLANOX HM 250D, from Tulco, Inc., of Ayer, Mass. Another exemplary micropowder is Teflon® MP 1200, available from DuPont Polymer Products Department, Wilmington, Del., and having an average particle diameter of about 4 μm.

Microfibers are another class of surface roughening agents that can be used in the coating compositions. An exemplary microfiber is a cellulose microfiber having an average diameter of about 4 microns and an average length of about 40 microns. Microfibers of longer lengths can also be used.

The methods of the present invention can comprise diluting a coating polymer solution or suspension prior to applying the solution or suspension to the nucleation column or to the inner surface of a drip chamber. The coating solution or suspension can be diluted to be between about 0.01% and 2% by weight coating polymer. Higher weight percentages of the polymer can be used.

Another method of applying a coating polymer solution or suspension comprises dip-coating the nucleation column or drip chamber into a polymer solution or suspension. Other coating methods can also be used, including spray coating, tumbling in solution, brush coating, padding, rinsing, spraying, fogging, transferring, painting, printing, stenciling, screen printing, pad printing, ink jet printing, injection molding, laminating, and doctoring. For simultaneously coating a large number of nucleation columns or drip chambers a tumbling method of coating, for example, can be used.

Dip coating can be used according to various embodiments, to apply the coating polymer from a solution of the polymer dissolved in a solvent or from a suspension of the polymer. After coating the polymer solution or suspension, the coating is allowed to dry and solvent or carrier is driven off.

According to various embodiments, the coating formulation is not a polymer solution or suspension but instead comprises a fluidized micropowder of the polymerization product of a monomer. The micropowder formulation can be applied to the inner surface of the drip chamber and melted to form a coating having practically any desired surface energy. According to various embodiments, the coating formulation comprises a fluidized micropowder of the polymerization product of a monomer, and at least one substantially non-perfluorinated resin. The micropowder and resin are applied to the surface of the nucleation column or drip chamber sidewall and then heated to melt the fluidized micropowder.

According to various embodiments, the coating polymer or coating monomer formulation of the invention is applied as a micropowder along with at least one of a curable resin and a non-curable resin. Preferably, the at least one resin is substantially non-perfluorinated, for example, non-fluorinated. Curable resins that can be used in formulations of micropowder coating material include epoxy resins, urethane resins, acrylate resins, and methacrylate resins. An exemplary resin having a high crosslink density is the epoxy novolac resin D.E.N. 439, available from Dow Chemical Co., Midland, Mich.

According to various embodiments, resins with low crosslink densities can be employed. An exemplary low crosslink density resin is the fusion solid EPON Resin 1004F available from Shell Chemical Company, Houston, Tex. EPON Resin 1004F is a bisphenol A epoxy resin having a melting point of about 100° C. Other EPON Resins from Shell Chemical Company can also be used, including 1001F, 1002F, 1007F, and 1009F, as well as the 2000 series powdered EPON Resins, for example, EPON Resins 2002, 2003, 2004, and 2005.

Non-curable resins that can be employed include powdered ethyl cellulose, powdered polyethylene, powdered polypropylene, and powdered polyvinylidenedifluoride. Cellulose acetate butyrate pellets can be jet milled and applied as a powder. Cellulose acetate butyrate is typically non-curable but can be cross-linked with peroxides.

The micropowders and resins can be formed, for example, by jet milling. The micropowders and resins are preferably particles having an average diameter of about 50 microns or less, for example, having average diameters of 10 microns or less. The powders can be electrostatically sprayed onto the inner surface of a drip chamber with or without a curing agent. Micropowders can also be prepared as latexes in aqueous suspensions, subsequently separated from the liquid phase, and dried.

In various embodiments, a surface is coated with a coating formulation comprising a fluidized micropowder of a polymerization product and a non-melting micropowder that does not melt at temperatures required for formation of the coating. The formulation is then heated or sintered to melt the fluidized polymerization product micropowder without melting the non-melting micropowder. The non-melting micropowder can be selected from the group consisting of Teflon® micropowders, Tefzel® micropowders, Kynar® micropowders, polyvinylidene difluoride micropowders, silica micropowders, and polypropylene micropowders.

According to various embodiments that involve forming coatings by melting micropowders, the coating formulations can be applied as a suspension to the inner surface of the drip chamber and subsequently dried prior to melting.

Another method of forming a nucleation column having abundant and improved nucleation sites involves pre-injecting or co-injecting a coating or exposed surface formulation prior to or during the laminar flow of molten materials injected into a mold or through an orifice to form the nucleation column. The pre-injected or co-injected coating formulation can comprise a thermoplastic resin and/or a thermosetting resin. The injectable coating formulation can comprise mixtures of reactive monomer, catalyst, and resin. The injectable coating formulation can comprise mixtures of molten prepolymerized monomer and microparticles, to form coatings exhibiting abundant, efficient nucleation sites. The injectable coating formulations can comprise mixtures of molten prepolymerized monomers, other resins, and microparticles, which are pre-injected or co-injected into or during the laminar flow of molten materials injected into a mold. The flow can instead be injected through an orifice to form a coating on the resultant nucleation column. The resulting surface can exhibit abundant and efficient nucleation sites and a low retention of biological samples.

According to various embodiments, the coating composition has a volume of hardenable resin that is less than the volume of microparticles in the composition. The microparticles can comprise inorganic substances, can be porous, and can comprise clusters of smaller particles. The microparticles can have an average particle size diameter of from about 1 micron to about 100 microns. In place of or in addition to the microparticles, the composition can comprise nanoparticles having an average particle size diameter of less than about 100 nanometers. The coating composition can include both microparticles and nanoparticles, for example, up to about 30% by weight nanoparticles based on the weight of the microparticles, up to about 10% by weight nanoparticles, or from about 5% by weight to about 10% by weight nanoparticles. Nanoparticles smaller than 30 nanometers can be used. The microparticles can be clusters of nanoparticles.

The hardenable resin of the composition can be hardened by radiation, by moisture, by oxidation, by the addition of a hardener or co-resin, by heat, by evaporation of a solvent, by a combination thereof, or the like. The hardenable resin can have a functionality of at least two, for example, a functionality of at least three. The hardenable resin can be at least one resin of an acrylate, an alkyd, a urethane, an isocyanate, an epoxy, a fluorocarbon, a silicone, a siloxane, a silicate, a ceramic, a metal, a polyester, a vinyl, an anhydride, a polyimide, a polyol, or a combination thereof. The hardenable resin can comprise polyhexamethylene diisocyanate, methylene bis hexane isocyanate, and/or an ethoxylated acrylic. The coating composition can include a hardenable resin, microparticles having an average particle size diameter of from about 1 micron to about 100 microns, and/or nanoparticles having an average particle size diameter of less than about 500 nanometers. The nanoparticles can have an average particle size diameter of less than about 100 nanometers. The microparticles can be made of polytetrafluoroethylene, a polytetrafluoroethylene copolymer, or a combination thereof. Such compositions can also include a volatile solvent, for example, an at least partially fluorinated volatile solvent. According to various embodiments, a composition of matter is provided that includes a volume of hardenable resin, and a volume of nanoparticles having an average particle size diameter of less than about 500 nanometers, wherein the volume of the nanoparticles is equal to or greater than the volume of the hardenable resin. The volume of the nanoparticles can be more than twice the volume of the hardenable resin. The nanoparticles can have an average particle size diameter of less than about 20 nanometers.

Another coating composition that can be used includes extremely fine hydrophobic micropowders having average particle size diameters of from about 1 to about 100 nanometers (nm), for example, in an amount of from about 1.0% by weight to about 30% by weight based on the total weight of the non-volatile components of the coating composition. Average particle sizes of from about 1 nm to about 50 nm are exemplary, as are average particle sizes of from about 1 nm to about 10 nm. For example, hard resin formulations including Dupont's ZONYL 5069, having nanoparticles with average particle size diameters in the range of from about 10 nm to about 100 nm, and added in an amount of about 10 percent by weight based on the weight of Dupont's ZONYL MP1000 in the formulation, can be used.

A process of improving a coating on the nucleation column or on the inner surface of a drip chamber is also provided that includes applying to the coating a film or layer onto and conforming to at least the interstitial surfaces of the coating. The film or layer can include a hardenable resin and a volume excess of particles. The film or layer can have a thickness of less than about 2 microns, or a thickness of less than about half of the average interstitial pore size diameter of the interstitial pores of the coating. The film can have a thickness of less than about 50 nanometers. The particles can have an average particle size diameter of less than about 100 microns. The film or layer can include nanoparticles having an average particle size diameter of about 500 nanometers or less.

A process of improving a surface having rough, porous, striated, embossed, particle-covered, or micropatterned features, is provided that includes applying to the surface a film or layer onto and conforming to the surface. The features have at least one width dimension of about 100 microns or less and are spaced about 100 microns or less apart. Features that have a height greater than about half their width dimension can be used. The features can be created using abrading, etching, machining, micromachining, photolithography, laser ablation, molding, embossing or any means that produces a micro-featured surface. The film or layer can include a hardenable resin and/or a volume excess of particles. The film or layer can have a thickness of less than about 10 microns, or a thickness of less than about half of the average distance between the rough, striated, embossed, particle-covered, or micropatterned features of the surface. The film can have a thickness of less than about 50 nanometers. The particles can have an average particle size diameter of less than about 100 microns. The film or layer can include nanoparticles having an average particle size diameter of about 500 nanometers or less. The resin to micropowder volume ratio can be, for example, from about one to about four. Hard epoxies, polyurethanes, and acrylics with high cross-link densities can be used and are exceptionally durable.

With reference FIG. 5, a transparent bubble catcher 50 is shown that includes a body 52, a cap 54, a bubble catcher 56, an inlet 58, and an outlet 60. Body 52 has an inner surface 62, the lower portion of which defines a blood-contacting surface 64. A blood tube 66 is in fluid communication with the interior of drip chamber 50 through inlet 58. Blood tube 66 can be sealed to cap 54 at inlet 58, for example, by sealant, adhesive, solvent bonding, a friction fit, an O-ring connection, co-molding, or the like. A hermetic seal can be provided. Cap 54 can be sealed to drip chamber body 52, for example, by sealant, adhesive, solvent bonding, a friction fit, an O-ring connection, co-molding, or the like. A hermetic seal can be provided. In addition to nucleation sites that may be provided by surface 64 of inner surface 62, a nucleation column 68 is provided extending from bubble catcher 56 and makes up a nucleation site-providing feature. Nucleation column 68 can be formed to include, or treated to provide, nucleation sites on the outer surface thereof. Herein, when describing materials, coatings, and methods for forming nucleation column 68, the same materials, coatings, and methods can be used for forming nucleation sites on blood-contacting surface 64 or the entirety of inner surface 62.

Nucleation column 68 can be integrally formed with bubble catcher 56 or formed separately then connected to bubble catcher 56. Nucleation column 68 can be screwed into a threaded receptacle in bubble catcher 56, solvent-bonded to bubble catcher 56, or otherwise adhered or connected to bubble catcher 56 and can intersect with bubble catcher 56 at an intersection 84. Nucleation column 68 and bubble catcher 56 can be 3D-printed together or separately, co-molded, or molded together as a single, unitary, monolithic structure. Nucleation column 68 can have a distal tip 86 that can terminate above, at, or below the typical level of blood in drip chamber 50 during normal operation.

Drip chamber 50 is also connected to a pressure line 70 sealed to cap 54 and leading to a pressure transducer (not shown). A clamp 72 is provided on pressure line 70. Pressure line 70 is in fluid communication with the headspace in drip chamber 50 and, in operation, in fluid communication with the pressure transducer, to sense gas pressure within the headspace.

Drip chamber 50 is also connected to a medication line 74 sealed to cap 54 and through which medication, saline, or other liquids or substances can be introduced into drip chamber 50. A clamp 76 is provided to close-off medication line 74 when not in use. Luer or other connectors 80 and 82 can be provided on the ends of pressure line 72 and medication line 74, respectively, to sealingly connect them to other components such as a pressure transducer or an intravenous line.

The present invention includes the following aspects/embodiments/features in any order and/or in any combination:

1. A drip chamber for separating air from blood in a blood line, the drip chamber comprising:
   a hollow body having a top and a bottom;
   an inlet in fluid communication with the hollow body;
   an outlet in fluid communication with the hollow body at the bottom of the hollow body; and
   a nucleation column having an outer surface, wherein the hollow body is defined by a sidewall and has an interior, the sidewall has an inner surface, the nucleation column extends into the interior, the nucleation column has been formed with, or treated by a treatment to form, microfeatures in or on the outer surface that provide nucleation sites for nucleation and amalgamation of microbubbles in a liquid that contacts the outer surface.

2. The drip chamber of any preceding or following embodiment/feature/aspect, wherein the nucleation column comprises a material, a population of the microfeatures at the outer surface is greater than a population of the microfeatures at a surface of the same material but that has not been formed with, treated with said treatment to provide, the microfeatures.

3. The drip chamber of any preceding or following embodiment/feature/aspect, further comprising a bubble catcher in the bottom of the hollow body, the bubble catcher providing flow passages providing fluid communication between the interior of the hollow body and the outlet.

4. The drip chamber of any preceding or following embodiment/feature/aspect, wherein the nucleation column extends from the bubble catcher into the interior of the hollow body.

5. The drip chamber of any preceding or following embodiment/feature/aspect, wherein the treatment comprises a coating treatment and the outer surface of the nucleation column comprises a coating.

6. The drip chamber of any preceding or following embodiment/feature/aspect, wherein the treatment comprises at least one of machining the outer surface, chemically etching the outer surface, or applying a coating to the outer surface.

7. The drip chamber of any preceding or following embodiment/feature/aspect, wherein the treatment comprises applying a coating to the outer surface, and the coating comprises microparticles.

8. A drip chamber for separating air from blood in a blood line, the drip chamber comprising:
a hollow body having a top and a bottom;
an inlet in fluid communication with the hollow body; and
an outlet in fluid communication with the hollow body at the bottom of the hollow body,
wherein the hollow body is defined by a sidewall, the sidewall comprises a material and has an inner surface, the inner surface has been treated by a treatment to form microfeatures in or on the inner surface, a population of the microfeatures at the inner surface is greater than a population of the microfeatures at a surface of the same material but that has not been treated with said treatment, and the microfeatures provide nucleation sites for nucleation and amalgamation of microbubbles in a liquid that contacts the inner surface.

9. The drip chamber of any preceding or following embodiment/feature/aspect, further comprising a bubble catcher in the bottom of the hollow body, the bubble catcher providing flow passages providing fluid communication between an interior of the hollow body and the outlet.

10. The drip chamber of any preceding or following embodiment/feature/aspect, further comprising a nucleation column extending from the bubble catcher into the interior of the hollow body.

11. The drip chamber of any preceding or following embodiment/feature/aspect, further comprising a nucleation column inside the hollow body.

12. The drip chamber of any preceding or following embodiment/feature/aspect, wherein the treatment comprises a coating treatment and the inner surface of the hollow body comprises a coating.

13. The drip chamber of any preceding or following embodiment/feature/aspect, wherein the treatment comprises at least one of machining the inner surface, chemically etching the inner surface, or applying a coating to the inner surface.

14. The drip chamber of any preceding or following embodiment/feature/aspect, wherein the treatment comprises applying a coating to the inner surface, and the coating comprises microparticles.

15. A method of making a drip chamber, the method comprising:
providing a drip chamber comprising a hollow body having a top, a bottom, an interior, a sidewall, an inner surface, and a nucleation column extending into the interior, the nucleation column having an outer surface;
treating the outer surface with a treatment, the treatment increasing a population of nucleation sites along the outer surface; and
capping the hollow body at the top thereof with a cap comprising a blood tube, to form a fluid communication between the blood tube and the interior.

16. The method of any preceding or following embodiment/feature/aspect, wherein the treatment comprises chemically etching the inner surface.

17. The method of any preceding or following embodiment/feature/aspect, wherein the treatment comprises applying a coating to the outer surface.

18. The method of any preceding or following embodiment/feature/aspect, wherein the treatment comprises machining the outer surface.

19. The method of any preceding or following embodiment/feature/aspect, further comprising:
providing a bubble catcher in the interior; and
connecting the nucleation column with the bubble catcher.

20. The method of any preceding or following embodiment/feature/aspect, wherein the connecting the nucleation column with the bubble catcher comprises integrally forming the nucleation column and the bubble catcher as a unitary, one-piece structure.

21. A method of making a drip chamber, the method comprising:
providing a drip chamber comprising a hollow body having a top, a bottom, an interior, a sidewall, and an inner surface;
treating the inner surface of the hollow body with a treatment, the treatment increasing a population of nucleation sites along the inner surface; and
capping the hollow body at the top thereof with a cap comprising a blood tube, to form a fluid communication between the blood tube and the interior.

22. The method of any preceding or following embodiment/feature/aspect, wherein the treatment comprises chemically etching the inner surface.

23. The method of any preceding or following embodiment/feature/aspect, wherein the treatment comprises applying a coating to the inner surface.

24. The method of any preceding or following embodiment/feature/aspect, wherein the treatment comprises machining the inner surface.

25. The method of any preceding or following embodiment/feature/aspect, further comprising:
providing an nucleation column within the interior; and treating the nucleation column with a treatment to increase a population of nucleation sites on the nucleation column.

26. The method of any preceding or following embodiment/feature/aspect, further comprising:

providing a bubble catcher at the bottom of the hollow body, wherein the nucleation column extends from the bubble catcher into the interior of the hollow body.

The present invention can include any combination of these various features or embodiments above and/or below, as set forth in the foregoing sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such specific ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A drip chamber for separating air from blood in a blood line, the drip chamber comprising:
    a hollow body having a top and a bottom;
    an inlet in fluid communication with the hollow body above the bottom of the hollow body;
    an outlet in fluid communication with the hollow body at the bottom of the hollow body; and
    a nucleation column having an outer surface comprising a material and being in the shape of an elongated rod,
    wherein the hollow body is defined by a sidewall that defines an interior space, the sidewall has an inner surface, the nucleation column extends upwardly from the bottom into the interior space, the inlet is above at least a portion of the nucleation column that is in the interior space, the nucleation column has been formed with, or treated by a treatment to form, microfeatures in or on the outer surface, the microfeatures provide an improved nucleation efficiency and nucleation sites for nucleation and amalgamation of microbubbles in a liquid that contacts the outer surface, and a population of the microfeatures in or on the outer surface is greater than a population of microfeatures in or on an outer surface of the same material but that has neither been formed with, nor treated with a treatment to form, microfeatures.

2. The drip chamber of claim 1, further comprising a bubble catcher in the bottom of the hollow body, the bubble catcher providing flow passages providing fluid communication between the interior space of the hollow body and the outlet.

3. The drip chamber of claim 2, wherein the nucleation column extends from the bubble catcher into the interior space of the hollow body.

4. The drip chamber of claim 1, wherein the nucleation column has been treated by a treatment to form the microfeatures, the treatment comprises a coating treatment, and the outer surface of the nucleation column comprises a coating.

5. The drip chamber of claim 1, wherein the nucleation column has been treated by a treatment to form the microfeatures, and the treatment comprises at least one of machining the outer surface, chemically etching the outer surface, or applying a coating to the outer surface.

6. The drip chamber of claim 5, wherein the nucleation column has been treated by a treatment to form the microfeatures, the treatment comprises applying a coating to the outer surface, and the coating comprises microparticles.

* * * * *